(12) United States Patent
Hudson

(10) Patent No.: US 6,546,793 B2
(45) Date of Patent: Apr. 15, 2003

(54) METHOD FOR MANUFACTURING CONCRETE

(75) Inventor: Barry Philip Hudson, Richmond, VA (US)

(73) Assignee: Aggregate Research Industries, Richmond, VA (US)

( * ) Notice: Subject to any disclaimer, the term of this patent is extended or adjusted under 35 U.S.C. 154(b) by 0 days.

(21) Appl. No.: 10/102,439

(22) Filed: Mar. 19, 2002

(65) Prior Publication Data

US 2002/0121133 A1 Sep. 5, 2002

Related U.S. Application Data

(63) Continuation of application No. 09/487,809, filed on Jan. 20, 2000, now Pat. No. 6,379,031.

(51) Int. Cl.$^7$ .......................... G01N 15/02; G01F 11/00
(52) U.S. Cl. ........................ 73/149; 73/865.5; 209/237
(58) Field of Search ................................ 73/149, 865.5, 73/863.23, 863.21, 866; 209/237; 366/8, 2, 16, 19

(56) References Cited

U.S. PATENT DOCUMENTS

| | | | | |
|---|---|---|---|---|
| 1,863,291 A | * | 6/1932 | Weston | 209/237 |
| 2,782,926 A | * | 2/1957 | Saxe | 209/237 |
| 3,439,800 A | * | 4/1969 | Tonjes | 209/237 |
| 3,545,281 A | * | 12/1970 | Johnston | 209/237 |
| 3,690,183 A | * | 9/1972 | Livingood | 73/865.5 |
| 4,381,669 A | * | 5/1983 | Peters | 209/237 |
| 4,519,244 A | * | 5/1985 | Meloy | 209/237 |
| 4,704,911 A | * | 11/1987 | Meloy | 209/237 |
| 5,059,310 A | * | 10/1991 | Fischer et al. | 209/237 |

FOREIGN PATENT DOCUMENTS

CN 1073525 * 6/1993

* cited by examiner

Primary Examiner—Tony G. Soohoo
(74) Attorney, Agent, or Firm—John H. Thomas, P.C

(57) ABSTRACT

A method for selecting proportions of aggregate for incorporation into concrete comprises several steps. First, a maximum aggregate size for a specific application is determined. A sample of the maximum size aggregate is loose poured into a container. The percentage voids in that sample is then calculated. An amount of smaller sized aggregate equal to approximately the volume of percentage voids calculated earlier is added to the sample until a reduced volume of voids in the mixed sample is achieved. Finally, the amounts of aggregate determined to have the reduced volume of voids in the mixed sample are used in a concrete mixture.

9 Claims, 1 Drawing Sheet

METHOD FOR MANUFACTURING CONCRETE

This application is a continuation of U.S. application Ser. No. 09/487,809 filed on Jan. 20, 2000 now U.S. Pat. No. 6,379,031.

This invention relates to an improved method for proportioning concrete materials in order to obtain an optimum proportion of the concrete mix components. The invention includes also the evaluation of aggregate and the optimum mix proportioning of aggregate to be incorporated in concrete.

BACKGROUND OF THE INVENTION

In conventional concrete mix design procedures, various assumptions are made about the characteristics of the aggregates that will be incorporated in the concrete mix. When characterizing an aggregate, for instance, the things that influence the way the aggregate performs in concrete are aggregate size, aggregate shape, and aggregate surface texture as well as any deleterious substances or materials present, or adhering to the aggregates. These properties influence the way that the aggregate packs together in a matrix, the amount of bond potential between aggregate particles and cement paste, and the water demand of the concrete to achieve a requisite fresh concrete workability.

Existing methods for measuring the size of a given aggregate include grading the aggregate particles by passing a sample of aggregates over a standard series of sieves that have square apertures of a specific size. The mass (weight) of materials retained on a given sieve size is recorded and expressed as a percentage of the total mass (weight) of the sample being sieved or percent retained. Typically, the result of each of these tests as a percent retained is subtracted from the former sieves' passing starting with the largest sieve through which 100% passes. This test is termed a percent passing grading or gradation or sieve analysis for the entire sample. The main drawback of this sieve analysis or grading test is that the apertures used in the standard sieves or screens are specified as square. The measured dimension of the aggregate that passes through the sieve is the middle size dimension or axis. A sieve does not measure the least or the greatest dimension. Because aggregate particles are irregular in shape, it is probable that the same square aperture will allow a flat or elongated particle to pass through the diagonal of the aperture and give a false measurement of the median dimension that is supposed to be measured.

Unfortunately, most existing mix design procedures utilize only the grading or sieve analysis data to characterize the size distribution of aggregates. This results in an inaccurate measure of the particle size distribution, because of the multitude of shapes that can give an "apparent" particle size. This inaccuracy in measurement is also seen in actual test running and batch analysis. For instance, two different aggregates having identical gradations can often yield different qualities of concrete. In summary, therefore, the sieve analysis is not the most effective for characterizing the size of aggregates for a concrete mixture.

Particle shape is another important characteristic to take into account when looking at proportioning the aggregates correctly in a concrete mix design. Currently, test methods that are used to determine particle shape are limited to a two dimensional test to simply conclude whether or not the aggregate is flat or elongated. This shape determination (measuring length and width) is made by expressing the percentage of mass of the sample that does not fit into a given ratio of the total sample. For example, if a permissible range depends on a percent by weight which must be less than a ratio of 5 to 1 (maximum dimension to minimum dimension), then the test does not accurately express the degree of misshapenness. For instance, in the example of an acceptable ratio of a percent by weight of less than 5 to 1, all the particles could have a ratio of 4.99 to 1.0 and therefore be considered a 100% pass rate while a sample having all particles with a ratio of 5.01 to 1.0 would have a 100% fail rate. In reality, these materials would most likely behave identically in a concrete mix.

Aggregate surface area and texture are also important attributes for determining the performance of a concrete mixture in the plastic and hardened states. The impact of these attributes on the concrete increases as the nominal size of the aggregate decreases. In the finer aggregate size fraction however, there is a critical specific surface value where this relationship diminishes. When the fine aggregate particles approach the size of the cement particles (less than 150 microns), the apparent influence of the high specific surface is minimized.

Also, in conventional test methods, a characterization of the fine aggregate portion is made using a value called the fineness modulus. The fineness modulus, or FM, for the fine aggregate portion of the mix is the sum of the percentage of the materials cumulatively retained, beginning at about the 9.5 mm sieve down to and including the 100 mesh sieve or 150 micron size. It is possible to have different gradations representing the same FM value, and hence this value can be misleading as to the representation of the overall particle size distribution of fine aggregate material. Especially important is the use of the fine aggregate FM to determine the volume of the coarse aggregate to be used in the mix.

Also, current concrete mix proportioning relates to the way various densities and voids calculations are made with respect to given aggregate samples. These samples are typically "rodded" whereby the sample is compacted during the mix proportioning calculation process. This is an unrealistic method, because the aggregate that is incorporated into the concrete will not have the same density as an artificially compacted sample. The rodding technique, therefore, renders the entire mix proportioning process as potentially inaccurate.

SUMMARY OF THE INVENTION

Accordingly, it is object of the present invention to overcome the foregoing drawbacks and provide a method for mixing concrete to obtain an optimum proportion of the concrete mix components including an optimum mix proportioning of the aggregate to be incorporated in the concrete.

In one embodiment, the method for selecting proportions of aggregate for incorporation into concrete comprises a series of steps. A maximum aggregate size for the specific application is determined. A sample of the maximum aggregate size is loose poured into a container and the percentage voids in the sample is calculated. An amount of smaller sized aggregate equal to approximately the volume of the percentage voids calculated is then added to the sample until a reduced volume of voids in the mixed sample is achieved. The amounts of aggregates determined to have the reduced volume of voids in the mix sample is then used in a concrete mixture. Also, the method may include repeating the steps of calculating the percentage voids and adding smaller sized aggregate to the mix sample. Further, cementitious material and water can be added to the aggregate to form a concrete mixture. Additionally, the maximum coarse aggregate size should be no greater than one-third of the lift height of the concrete to be poured, one-fourth of the nominal diameter of the pumping hose, and one half of the nominal spacing between reinforcement bars.

In another embodiment of the invention, a sample of aggregate may be evaluated by selecting a representative sample of the aggregate. For each stone in the sample, the greatest dimension of the stone is measured and recorded. Then, a template having different sized apertures cut into it is provided. Each stone in the sample is then passed through the apertures in the template until the stone is retained on the template. The measurement of the aperture on which the stone is retained is recorded. The recorded information is then used to calculate the volume of the aggregate stones in the sample.

In a still further embodiment of the present invention, a method of selecting aggregate for incorporation into a concrete mixture comprises only using an amount of aggregate whose total ultra-fines percentage content complies with the formula $$\left(A \times \frac{y}{3.15}\right) < (-300 \times B) + 2000.$$

In this formula, A equals the cementitious materials content of the concrete mixture in kilograms per cubic meter, B equals the total ultra-fines percentage content in the aggregate to be used in the concrete mixture by volume, and y equals the density of the cementitious material.

In a still further embodiment, a method of selecting aggregate for incorporation into a concrete mixture comprises using only an amount of aggregate whose total ultra-fines percentage content and methylene blue test values comply with the following formula: 0.08 C×D. In the foregoing formula, C equals the total ultra-fines percentage content by volume in decimal form and D equals the methylene blue test value of the aggregate to be used in the concrete mixture.

DETAILED DESCRIPTION OF A PREFERRED EMBODIMENT

Figure 1:
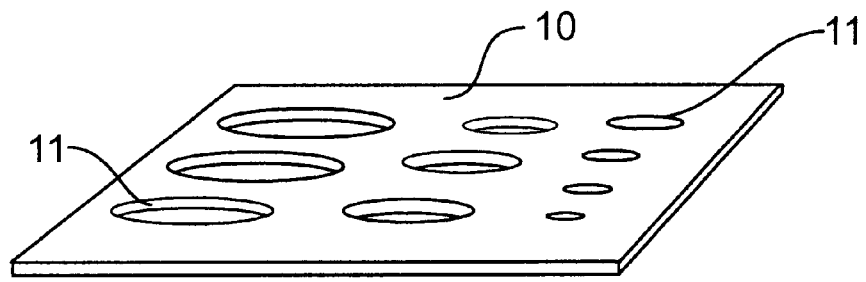
FIG. 1 is a perspective view of a template used to characterize aggregate according to one embodiment of the present invention.

It is a purpose of the present invention to improve and, if possible, optimize the mix design procedure by determining the maximum packing of the aggregate ingredients that produce a workable and acceptable concrete. This maximum aggregate packing or volumetric optimization will assist to minimize the paste portion of the mix which contains the most expensive ingredients resulting in an acceptable concrete quality in both its plastic (fresh) and hardened states. The goal is to obtain an acceptable concrete at a lower total cost. In general, the most expensive component in concrete is the cementitious material, followed by the aggregates, and finally any optional chemical admixtures. Therefore, a mix proportion that includes more aggregate, i.e., less cementitious materials, is more economical than a proportion that calls for more cementitious material.

Aggregate Proportion Selection

The present invention includes blending the aggregate portions of the concrete mix to minimize the amount of voids between all of the concrete ingredients (with the exception of entrained air), thereby decreasing the amount of paste (cementitious materials and water) necessary to bind those components together to form concrete. More specifically, the mix design of the present invention is aimed at obtaining the highest volume of aggregates in a concrete mix so that the volume of finer materials required to get a solid workable volume of concrete is minimized.

The first step of the process is to develop the proportions of coarse aggregates to be incorporated into the concrete mixture. Coarse aggregates are known in the industry to be +4.75 mm material (4 mesh). Aggregates smaller than 4.75 mm (4 mesh) are referred to as fine aggregate or sands. Also, typically, only a limited number of aggregates will be available to a given concrete manufacturer. The availability and size of the aggregates will vary according to geography, rock geology, as well as the proximity of quarries and types of production processes. The type of stone which is used will often dictate the size of the crushed aggregate that is available. Therefore, this invention assumes that at least two or more sizes of aggregates will be available to a concrete mix designer. If there is only one size of aggregate available, then the ability to optimize the volumetric packing may be limited as no other aggregates are available to maximize the proportioning.

The strength and method of application of the concrete are conventionally specified to the concrete manufacture. This specification may require a particular maximum size aggregate. If the maximum size is not determined by specification, the end use of the concrete, together with the method of actually placing the concrete, can also dictate the maximum size of aggregate. For instance, the maximum size of aggregate should be no greater than about one-third the lift height of the concrete being poured. If the aggregate is larger than this, it would be possible for three particles to stack on top of each other and be thicker than the lift. Also, the size should be no greater than about one quarter the nominal diameter of a concrete pumping hose to be used. This helps prevent blockage of the hose. And the maximum size should be less than about one half the nominal spacing between reinforcement bars to help prevent the formation of pockets of air in the form being poured.

Once the maximum sized aggregate has been selected, a sample of that aggregate is loose poured into a sample container. The diameter of the container needs to be at least about 20 times larger than the middle sized dimension of the maximum sized aggregate. The middle sized dimension is the value at which 90% of the aggregate stones have a dimension less than that number. The height of the sample container should be at least about 1.5 times higher than the diameter of the container. (if the container size is substantially smaller in height or diameter, then there is too much interference at the container wall because of particle interface). The aggregate is gently poured into the container so that each of the stones falls randomly and its relative orientation is not unduly influenced by compression, tamping, compaction, or any other mechanical means. Once the container is full, the top is screeded (leveled) off to approximate as much as possible a level surface. The container is then weighed and from the specific gravity and container volume data, the percentage voids in the sample is calculated.

The foregoing percentage voids calculation takes into account all of the properties of the aggregate, as well as how it behaves in a packing situation. Although it is impossible to separate the specific values for particle size, surface texture, or particle shape, each of these attributes influences the volume of voids that are in the particular sample. The volumetric calculation of the percentage voids is substantively different from the conventional "unit weight" test that incorporates the compaction of the sample in order to arrive at a mixed proportion.

After measurement of the percentage voids of the first sample, a second aggregate is introduced to the sample and mixed with it. The amount of the second aggregate that is added is approximately equal to the percentage voids calculated in the first aggregate sample. For instance, if there are 40% voids in the first aggregate, then approximately 40% by volume of the next finest aggregate is introduced into the sample and mixed with it. The percentage voids test is then repeated and voids content calculated. This voids calculation will be conducted for each succeeding finer aggregate. This successive procedure will act to minimize the voids during each addition of aggregate to be incorporated into the concrete mixture.

The number and size of aggregates used will depend upon the specification of a job and the availability of the aggregate. In many conventional concretes, only two or three aggregates may be used. Obviously, in some applications, four or more can be incorporated into the concrete mixture.

Also, the foregoing volumetric evaluation can be further optimized when adding additional aggregates to the sample mixture. Specifically, rather than just adding the amount of aggregate equal to the percentage voids, further testing is done by using a bracketing technique such as adding, for instance, an additional 10% of the smaller aggregate or 10% less of the smaller aggregate to the mix sample. In the instance of our 40% voids, a sample of 44% or a sample of 36% or both of the smaller aggregate is added, mixed and tested for percentage voids. Depending on which calculation obtains the lower voids content, then further testing may be done to precisely reach an accurate, optimum blend of aggregates to obtain a concrete mix proportion with the highest proportion of aggregates available to obtain the lowest percentage of voids.

Once the coarse aggregate fraction of the concrete mix is proportioned as explained above so that the voids content is as low as it can be in the loose poured state, the next step is to determined the proportion of the fine aggregates that may be incorporated in the concrete mixture. In this step of the proportioning analysis, the sample mixture will contain all of the concrete ingredients so as to form a plastic mixture. The fine aggregates cannot be combined with larger aggregates and evaluated in a dry mixture, because the larger aggregates and the finer materials tend to separate in a container. When evaluating the optimum mixture that contains fine aggregates, therefore, the analysis changes slightly from a voids calculation to a density calculation. In other words, the complete concrete mixture that includes water and cementitious materials does not have any voids (aside from entrained and/or entrapped air). Nevertheless, the density of fine aggregates is virtually always greater than the density of the mixture of water and cementitious materials; therefore, a mixed sample that has greater density contains less void volume between aggregate particles than a comparative sample with a lower density. In order to make sure the density calculation of the complete concrete mixture sample is as accurate as possible, the sample may be vibrated, mixed, compacted, or otherwise agitated to minimize or remove air pockets and bubbles.

As with the earlier-noted procedures with larger aggregates, the amount of fine aggregate equal to the percentage voids of the complete, larger aggregate mixed sample is added to the aggregate mixture. Then, water and cementitious materials are simply added to reach the desired workability of the fresh concrete mixture. The fine aggregate percentages can also be altered using a bracketing technique as per the larger aggregate proportioning until the highest density concrete is determined.

Once the optimum density of the concrete is determined, this optimum mixture must be compared with the maximum and/or minimum cementitious material content and water/cementitious material ratios that are specified for a given application. In other words, the optimally proportioned concrete with respect to aggregate content may require water and cementitious material ratios that are outside the parameters of the given specification. Also, where a maximum or minimum cementitious content is specified, and too much water and cementitious material (or not enough) are necessary to obtain a workable concrete, the optimally proportioned concrete with respect to aggregate content may also be outside the parameters of the given specification. In either case different aggregates must be considered for the concrete in order to meet the specification and have optimally proportioned concrete with respect to aggregate content.

Aggregate Characterization

The foregoing test method for aggregate proportioning can be used in any concrete proportioning, but would be conventionally used when evaluating aggregates as they are normally screened through a square sieve screen by a conventional quarry or crusher. In some cases, however, when seeking to calculate proportions for ultra high performance concretes, an extremely tight packing between aggregates may be required. In this situation, data on the sphericity and roundness of the particles becomes important. It is important to have the largest, best shaped, equidimensional aggregate possible, since the larger the particle, the smaller the surface area of the aggregate particle. Therefore, the larger the aggregate particle, the less the specific surface for the given volume occupied by that mass of aggregate. The less the surface area of aggregates, then the less the amount of water would be required to obtain the same performance attributes in a fresh concrete mixture.

A more accurate aggregate test may be used to measure the sphericity and roundness and size of coarse aggregate to be incorporated in concrete. This test includes taking a representative sample of, for instance, a coarse aggregate (at least 200 stones) and performing measurements on each stone in that sample. Each stone is measured with a caliper, and the greatest dimension of the stone is measured and recorded. Then, each stone is passed through an aperture in a template and the aperture size is recorded at the largest aperture that the stone does not pass through. Depending on the particle size recorded in these measurements, a more accurate particle size distribution can be calculated for the volumetric analysis. From the foregoing information, the volume of the specific particle can be calculated. By recording the information of a representative sample of stones, an accurate statistical analysis can be performed to more accurately characterize the stones in a given sample.

The template that is used in this new test preferably consists of a sheet of metal, approximately 3 mm thick, with circles cut into it. The circles begin in size at the top size aggregate that is being tested, and each circle reduces in diameter by 0.5 mm until you get to 5.0 mm. Alternatively, the area of the circles may decrease by fifteen percent of the area of the circle of the next larger size. While circles are preferably used, other shapes of the apertures in the template, including, for instance, ovals, may be used when certain attributes may be desirable. Also, at the preference or discretion of the person conducting the test, an oval aperture may result in a more accurate calculation of volumetric size of a given stone. Also, the specific diameter of the aperture size for each aperture relative to the other apertures may be varied at the discretion of the person performing the testing, or the person fabricating a test template. An advantage of the round aperture is that it is a more accurate measure when used to calculate volume as compared with the square apertures in a standard screen sieve. A template 10 having different diameter apertures 11 is demonstrated in FIG. 1.

Figure 2:
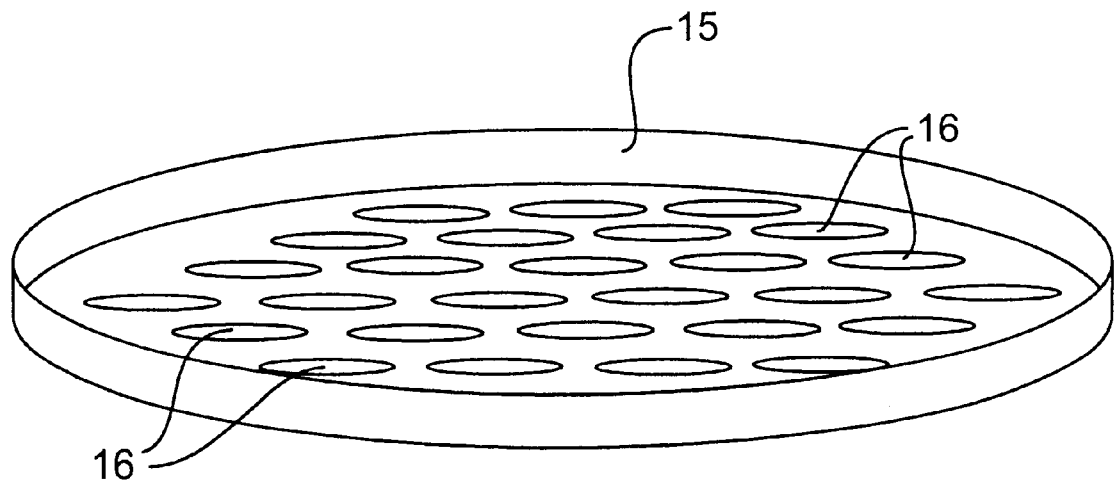
FIG. 2 is a perspective view of a template according to another embodiment of the present invention.

Alternatively, rather than just using a single template with different-sized apertures, it is also possible to have several templates, each with a plurality of the same-sized apertures in it. These templates having the same-sized apertures may be used separately or in a series when evaluating different samples. A template 15 having uniform sized apertures 16 is illustrated in FIG. 2.

The characterization of the sample based on the foregoing tests presents a more accurate model to estimate volume and specific surface as compared with the square openings present in the standard screen. From this information, the ideal volume of the aggregate particles to fit between the voids left by coarser particles may be calculated. In this way, the analysis literally characterizes the voids between the aggregates rather than the aggregates themselves in order to determine optimum mix proportions.

Ultra-Fines Analysis

Another step in the proportioning exercise is to evaluate the level of ultra-fine particles that may adversely affect the concrete performance. "Ultra-fines" are materials that are generically referred to as 75 microns (−200 mesh) or less. Therefore, once the materials have been proportioned in order to obtain maximum density of aggregates, and once the material satisfies the cementitious content requirement and water to cementitious material ratios, then the total volume of ultra-fines must be evaluated to make sure that they are not excessive.

Currently, conventional wisdom and many specifications mandate a maximum percentage of ultra-fines in the sand (fine aggregate) fraction of the concrete mixture only. These permissible limits are discussed in ASTM C33. Further, it is conventional wisdom to treat natural sands and manufactured sands in the same manner with respect to ultra-fines analysis. In fact, natural and manufactured sands are typically very different with respect to particle shapes and sizes and with respect to the impurities contained within them. The convention of only looking at the amount of ultra-fines in the sand fraction (and treating all "sands" the same) is potentially inaccurate and inefficient. Instead, the amount of ultra-fines must be evaluated in the context of the entire concrete mixture.

The ultra-fines analysis is even more complicated, because the maximum amount of permissible ultra-fines will vary with the cementitious materials content of the concrete. The formula to calculate maximum permissible ultra-fines content, therefore, varies according to both ultra-fines and cementitious materials content and according to the density of the cementitious material:

A=cementitious material content (kg/m³)

B=ultra-fines content by volume (% of entire aggregate fraction passing −75 micron mesh)

y=density of the cementitious materials (kg/m³)

$$\left(A \times \frac{y}{3.15}\right) < (-300 \times B) + 2000$$

For example, assuming a cement content of 200 kg per cubic meter and a total volume of −75 micron of 5.5% (and a cementitious material density of 3.15 kg/m³), the formula would be the following: 200 kg/m³<−300×(5.5)+2000 (or 200<350), therefore the ultra-fines content is acceptable. If the ultra-fines content in the aggregate was 6.5% and the same cement was used, the answer would have been 200>50, therefore there are too many ultra-fines, and new materials or proportions must be used. Based on this example, when mixing 200 kg/m³ of cement in a concrete, the maximum amount of permissible ultra-fines in all of the aggregate is about six percent.

Impurities Analysis

A still further step in the concrete proportioning analysis is to look not just at the quantity of the ultra-fines, but also at the deleterious materials or impurities, for instance organics, clay particles, etc., that may exist in the ultra-fines. These impurities can affect the performance of the overall concrete mixture.

Similar to the analysis of ultra-fines, conventional wisdom and specifications mandate a maximum amount of impurities in the sand (fine aggregate) fraction only. Typically, only the natural sands are tested. The measure of impurities is the C837-81 (1992) ASTM Standard Test Method for Methylene Blue Index of Clay.

Rather than just look at the sand (fine aggregate) fraction, the entire aggregate fraction must be considered. In other words, the impurities in the ultra-fines in both the coarse and fine aggregates (natural and manufactured) must be measured. Therefore, the methylene blue value is measured for all the ultra-fines in the concrete mixture.

In order to calculate a maximum value of impurities that may be present, the methylene blue values and the total fines percent volume are incorporated into the following formula:

C=% ultra-fines (by volume) in all aggregate represented as a decimal

D=methylene blue value of ultra-fines from all aggregate 0.08 C×D

Any time the amount of ultra-fines and level of impurity in the ultra-fines is too high, or specifically the multiple thereof is over 0.08, then the concrete mixture is not acceptable.

For example, if an aggregate sample (coarse and fine aggregate) contains 10% ultra-fines (10% passing the −75 micron sieve), and the ultra-fines have a methylene blue value of 0.4, then the above formula results in the number of 0.04. This is less than or equal to 0.08. Therefore, the amount of impurities is acceptable. Also, if there are several aggregates to be used, the methylene blue value of each aggregate fraction times the percent ultra-fines by volume in each fraction times the relative volumetric proportion of that aggregate fraction can be calculated. This partial value can be added to the same partial value for each aggregate fraction. In this way, for instance if the methylene blue value and ultra-fines percentage are known for several different aggregate fractions, then hypothetical mixtures may be compared to see whether they meet the guidelines of this test.

As is evident to those of skill in this art, this impurity formula may also be used to select which and how much of a particular type of aggregate may be used given the characteristics of other aggregates available for or already in a given mixture.

Although the invention has been described in detail for the purpose of illustration, it is to be understood and appreciated that such detail is solely for the purpose of example, and that other variations, modifications and applications of the invention can be made by those skilled in the art without departing from the spirit and scope of the invention.

What is claimed is:

1. A method of evaluating a sample of aggregate comprising the following steps:
    a) selecting a representative sample of aggregate,
    b) for each stone in the sample, measuring the greatest dimension of the stone and recording the measurement,
    c) providing a template having different sized apertures cut into it,
    d) for each stone in the sample, passing the stone through the apertures in the template until the stone is retained on the template and then recording the measurement of the largest aperture in which the stone is retained, and
    e) using the recorded information to calculate the volume of the aggregate stones in the sample.

2. The method according to claim 1, wherein the apertures are circles.

3. The method according to claim 2, wherein each circular aperture has a diameter that is at least 0.5 mm different from the diameter of the next closest size aperture diameter.

4. The method according to claim 2, wherein the smallest diameter of any of the circular apertures is 5 mm.

5. The method according to claim 1, wherein the representative sample of aggregate comprises at least 200 stones.

6. A method of evaluating a sample of aggregate comprising the following steps:
    a) selecting a representative sample of aggregate,
    b) for each stone in the sample, measuring the greatest dimension of the stone and recording the measurement,
    c) providing a plurality of templates having different sized apertures cut into them,
    d) for each stone in the sample, passing the stone through the apertures in the templates until the stone is retained on a template and then recording the measurement of the largest aperture in which the stone is retained, and
    e) using the recorded information to calculate the volume of the aggregate stones in the sample.

7. The method according to claim 6, wherein the apertures are circles.

8. The method according to claim 6, wherein each template has the same-sized apertures.

9. The method according to claim 6, wherein the representative sample of aggregate comprises at least 200 stones.

* * * * *